United States Patent [19]
Sherk

[11] 3,952,052
[45] Apr. 20, 1976

[54] PROCESS FOR PRODUCING ALKALI METAL SALTS OF AROMATIC POLYCARBOXYLIC ACIDS
[75] Inventor: Fred T. Sherk, Bartlesville, Okla.
[73] Assignee: Phillips Petroleum Company, Bartlesville, Okla.
[22] Filed: Apr. 15, 1974
[21] Appl. No.: 460,939

[52] U.S. Cl. .............................. 260/525; 260/515 P
[51] Int. Cl.² .................. C07C 51/52; C07C 51/01
[58] Field of Search ..................... 260/525, 515 P

[56] References Cited
UNITED STATES PATENTS

| | | | |
|---|---|---|---|
| 2,904,587 | 9/1959 | Johnson et al. | 260/515 P |
| 2,913,488 | 11/1959 | Blaser et al. | 260/515 P |
| 3,023,234 | 2/1962 | Schutt et al. | 260/251 R |
| 3,042,717 | 7/1962 | Schenk | 260/522 |
| 3,093,683 | 6/1963 | Raecke et al. | 260/515 P |
| 3,096,366 | 7/1966 | Smith | 260/515 P |
| 3,751,457 | 8/1973 | Marwil | 260/515 P |

Primary Examiner—Anton H. Sutto

[57] ABSTRACT

The effluent of a disproportionation reactor comprising alkali metal salts of aromatic polycarboxylic acids and a dispersant is flash evaporated so as to separate the effluent into a vapor phase comprising the vaporized dispersant and a solid phase comprising the alkali metal salts of the aromatic polycarboxylic acids.

9 Claims, 1 Drawing Figure

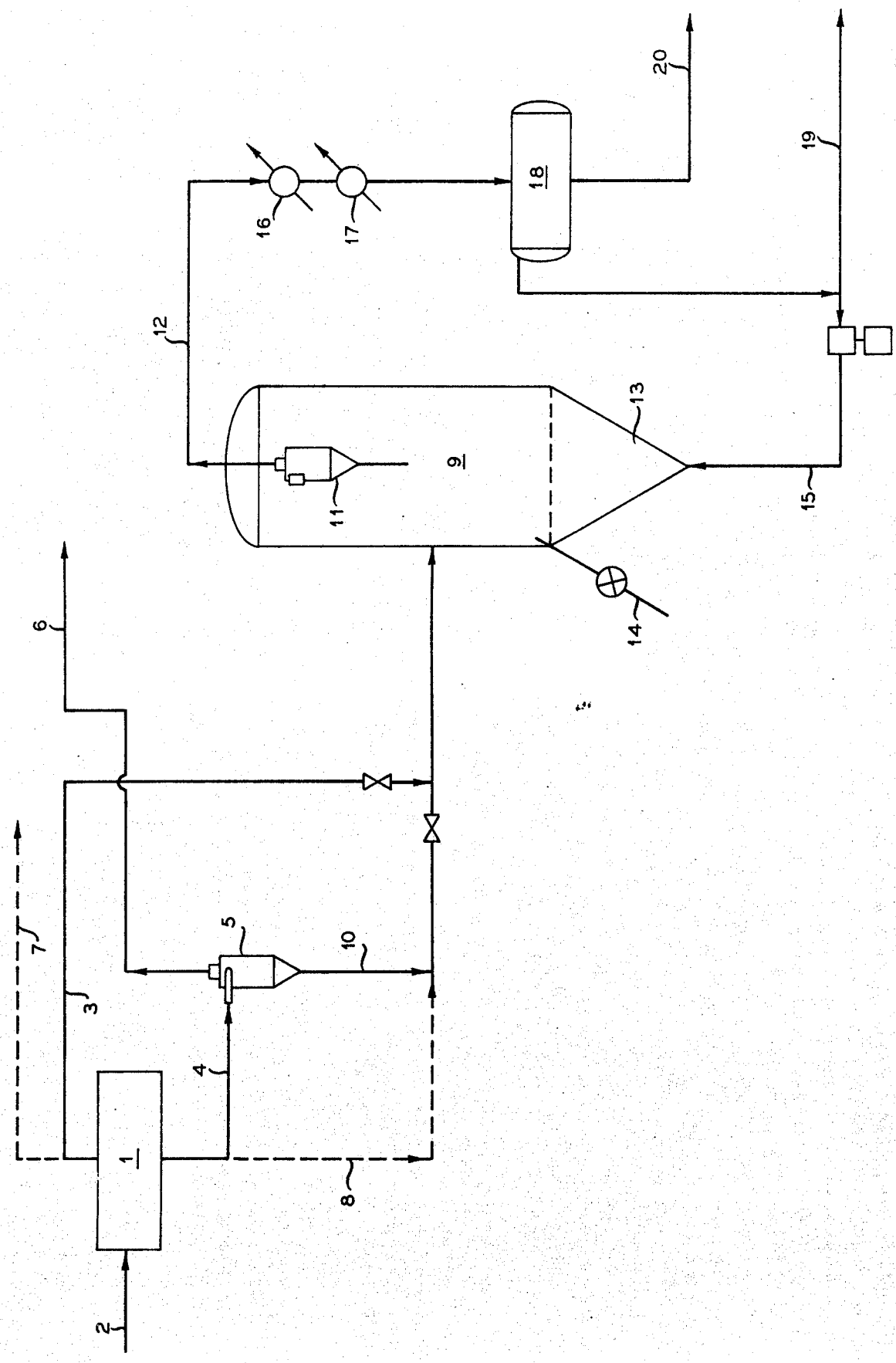

PROCESS FOR PRODUCING ALKALI METAL SALTS OF AROMATIC POLYCARBOXYLIC ACIDS

This invention relates to the art of production of aromatic polycarboxylic acids, such as terephthalic acid. These acids are used as monomers in the production of various polymers such as polyesters or polyamides. One of the best-known polyesters in this class is polyethylene terephthalate.

BACKGROUND OF THE INVENTION

It is known in the art that aromatic carboxylates, such as potassium benzoate, when heated under pressure form aromatic polycarboxylates, e.g., dipotassium terephthalate and benzene. This disproportionation reaction can be advantageously carried out in the presence of a high-boiling aromatic dispersant, e.g., terphenyl.

Various methods for separating the dispersant from the aromatic polycarboxylates are broadly disclosed in the art, e.g., benzene extraction, evaporation, sublimation. The separation of the dispersant and the solids can also be effected by extraction with water at high temperature and pressure. This water extraction step is vulnerable to problems which are oftentimes associated with the settling and phase separation of large amounts of aqueous solutions mixed with large amounts of organic solutions. Evaporation or sublimation, on the other hand, is a slow and costly method, both with respect to the apparatus and to the energy necessary.

THE INVENTION

It is thus an object of this invention to provide an improved process for the production of alkali metal salts of aromatic polycarboxylic acids.

Another object of this invention is to provide a process for the production of alkali metal salts of aromatic polycarboxylic acids by improving the step of separating the dispersant used in the reaction for forming the alkali metal salt of the aromatic polycarboxylic acid from the solids produced by the reaction.

Other objects, aspects, features and advantages of this invention will be apparent to one skilled in the art from the following detailed description of the invention, the drawing, showing a schematic outline of an apparatus for carrying out the process of the present invention, and from the appended claims.

In accordance with this invention, I have now found that in a process for producing alkali metal salts of aromatic polycarboxylic acids wherein alkali metal salts of aromatic carboxylic acids are disproportionated to produce said alkali metal salts of aromatic polycarboxylic acids in the presence of a dispersant, the slurry formed during the said disproportionation can be readily separated into a first portion comprising said alkali metal salts of polycarboxylic acids and a second portion comprising the dispersant by suddenly lowering the pressure of said slurry so as to flash evaporate the dispersant.

More particularly, I have found that by suddenly lowering the pressure of the hot effluent slurry coming from the reaction zone wherein the disproportionation of the aromatic alkali metal carboxylate resulting in aromatic alkali metal polycarboxylate takes place, the sensible heat of the effluent slurry effects a rapid evaporation of the dispersant used in said reaction zone and that the solids comprising the alkali metal polycarboxylate can be thereafter readily recovered and the gaseous phase comprising the dispersant vapor can be withdrawn.

In one presently preferred embodiment of this invention, the hot effluent slurry coming from the disproportionation reaction zone is introduced into a concentration zone, preferably a solids-liquids separator such as a cyclone, thus increasing the solids content of the slurry and introducing the concentrated hot effluent slurry into the separation zone where the pressure of the slurry is suddenly lowered. This concentration step makes more sensible heat energy per unit of dispersant available, and the flash evaporation chamber can be built smaller. The dispersant, e.g., liquid terphenyl, withdrawn in this concentration step from the effluent slurry can be recycled to the reaction zone either directly or after being blended with catalyst or a feedstock, such as potassium benzoate. The hot dispersant can also be placed in heat exchange relationship with other process streams to conserve thermal energy.

There is thus provided a process for producing alkali metal salts of aromatic polycarboxylic acids which comprises the steps of introducing alkali metal salts of aromatic carboxylic acids, a dispersant and a catalyst into a reaction zone, reacting said components at elevated temperature and high pressure so as to form a slurry comprising said alkali metal salts of said aromatic polycarboxylic acids and said dispersant, separating said dispersant and said alkali metal salts of said aromatic polycarboxylic acids by suddenly lowering the pressure of said slurry in a separation zone so as to evaporate the dispersant, and withdrawing the evaporated dispersant from the separation zone. It is, in accordance with a further embodiment of this invention, preferred to introduce the hot slurry coming from the reaction zone together with the hot gaseous compounds of the reactor into the separation zone where the pressure of the slurry is suddenly lowered. Thus, a gaseous effluent stream and the slurry coming from the reaction zone can be combined and then introduced into the flash evaporation zone.

In accordance with still another embodiment of this invention, the slurry coming from the reaction zone is treated in a concentration zone so as to increase the solids content of said slurry. This concentrated slurry is then combined with a gaseous effluent coming from that reaction zone, and the resulting mixture of concentrated slurry and gaseous effluent is then passed into the separation zone for suddenly lowering the pressure of the slurry in order to flash evaporate said dispersant. This embodiment provides the largest amount of sensible heat energy per unit of volatizable dispersant.

In each of these embodiments the sensible heat of the hot reactor effluents is used to provide the thermal energy to evaporate the aromatic dispersant in the flash evaporation zone. No additional heat energy need be applied. In addition, the resulting stream of evaporated aromatic dispersant can subsequently be advantageously employed for heat exchange purposes, e.g., to generate both low pressure and high pressure process steam.

In the process for producing dipotassium terephthalate and hence terephthalic acid, solid particles of potassium benzoate dispersed in a dispersant such as terphenyl are disproportionated to dipotassium terephthalate and benzene using a catalyst such as solid zinc benzoate. Carbon dioxide is also fed to the reactor as a reaction modifier.

Typical operating conditions for the disproportionation reactor are disclosed in U.S. Pat. Nos. 3,751,457 and 3,781,341. Temperatures in the range of about 825° to 860° F. and pressures of about 700 to 1000 psia are preferred. The residence time of the components in the reaction zone is about 0.3 to 1 hour. The typical conversion level of potassium benzoate is about 90 percent and the selectivity to dipotassium terephthalate is about 85 percent. The aromatic dispersant, e.g., terphenyl, is present in the reaction slurry in an amount of 25 to 80 percent, preferably 60 to 75 percent, by total weight of the slurry.

The hot effluent slurry from the disproportionation reactor comprises major amounts of the dispersant and alkali metal salts of aromatic polycarboxylic acids together with smaller amounts of other materials. Thus, in a typical slurry, major amounts of terphenyl and dipotassium phthalates are present together with minor amounts of potassium benzoate, zinc oxide, benzene, potassium carbonate, and other residues. The gaseous portion in the disproportionation reactor comprises essentially carbon dioxide and benzene vapor.

It is advantageous to use a dispersant for the disproportionation reaction which is selected from the group consisting of biphenyl, terphenyl, quaterphenyl, binaphthyl, isomers thereof and mixtures of these compounds. Among said dispersants, terphenyl is presently the preferred dispersant.

The disproportionation reaction is carried out either batchwise or continuously in any suitable reactor or sequence of reactors and related equipment in which the desired temperature and pressures can suitably be maintained and which can adequately be used for charging, stirring, and discharging of slurries. In addition to a lower outlet for a slurry discharge, the reactor can be fitted with an upper outlet for discharging gaseous products either intermittently or continuously.

In the embodiment of the present invention employing a solids concentration step for withdrawing a portion of the dispersant in liquefied state from the effluent slurry coming from the reaction zone, said slurry is conducted into a solids-liquids separator under conditions which retain, as closely as possible, the temperature of the slurry. For this concentration step any solids-liquids separation device, such as a solids-liquids cyclone, can be used which is capable of being operated at such elevated temperatures as 900° F. and at pressures up to 1000 psia. In said concentration step about 10 to about 60 percent of the dispersant, e.g., the terphenyl, can be removed as a liquid from the slurry coming from the disproportionation reaction zone and can be recycled into said reaction zone.

The separation zone can comprise any suitable flash evaporation chamber and related means by which feeds are sprayed into a chamber which is maintained at a reduced pressure. The chamber contains means for removal of the hot dispersant vapor as an overhead stream from the flash chamber. It is presently preferred to disengage the dispersant vapor from the entrained solids by means of a solids-gas cyclone. The lower portion of the flash chamber can provide a storage tank for the accumulation of the essentially dried salts and other solids. The chamber can also contain an outlet near its lower portion for removal of the solids, either intermittently or continuously, for further processing.

As an aid to the flash evaporation and in order to maintain the solids in the lower portion of the flash evaporation chamber serving as a storage tank in a mobile or partly fluidized state, it is presently preferred to pump a stream of recycled vapors or gases, such as a mixed stream of benzene vapor and carbon dioxide, into the bottom of the flash evaporation chamber and solids storage tank either continuously or intermittently. This stream should be sufficient to provide some fluidizing action on the solids, but it should not be so great as to unduly cool the flash evaporation chamber or otherwise impede the flash evaporation of the terphenyl. The pressure at which the flash evaporation chamber is maintained will be that which is sufficient to suddenly vaporize a substantial amount of the dispersant using only the sensible heat provided by the feed to the flash evaporation chamber. The pressure, thus, can vary with the liquid content of the feed and with the temperature and pressure of the feed. Ordinarily the pressure in the evaporation chamber will be in the range of 10 to 100 psia, preferably 20 to 50 psia. The pressure drop is preferably in the range of 500 to 900, more preferably 700 to 800 psia.

The dispersant vapor which exits the upper portion of the separation zone wherein the pressure of the slurry introduced is suddenly lowered is preferably recycled to the process. Preferably, this dispersant vapor is first placed into heat exchange relationship with other process streams to conserve heat energy. Thus, the dispersant vapors can be utilized to produce both high-pressure and low-pressure process steam. Once liquefied, the dispersant can be combined with any other dispersant streams, e.g., those produced by a slurry concentration step.

Gaseous or vaporous materials, such as carbon dioxide or benzene, produced by the disproportionation reaction can be withdrawn from the separation zone together with the dispersant and can be separated from the dispersant at any convenient point and subjected to further processing. A portion of these gaseous or vaporous materials can be recycled as a fluidizing gas to the separation zone, i.e., the flash evaporation chamber. Benzene can be isolated by convenient means, such as fractionation, and removed from the process whereas carbon dioxide can be recycled to the disproportionation reaction zone.

The following description of a specific example of the invention in connection with the drawing will enable a person skilled in the art better to understand and practice the invention. The drawing is described in terms of preparing dipotassium terephthalate using terphenyl as a dispersant. The specific details given in the following, however, are not intended to limit the scope of this invention.

As shown in the drawing, there is provided a disproportionation reactor 1. Into this reactor 1 potassium benzoate, zinc benzoate, carbon dioxide and terphenyl are fed through inlets, all represented by line 2. From the reactor 1 a gaseous and vaporous overhead effluent emerges via stream 3. The liquid slurry effluent of the reactor 1 flows, in the preferred embodiment, via stream 4 to a slurry concentration cyclone 5. From this cyclone 5 a stream 6 comprising hot liquid terphenyl is removed. This terphenyl can be further processed and recycled to the reactor 1. The gaseous effluent from the reactor 1, in one embodiment, can be passed via line 7 to a carbon dioxide and benzene recovery (not shown). Instead of using a concentration means, the liquid slurry effluent of the reactor 1 can also be directly fed via line 8 to a flash chamber 9. This line 8 can also be a bypass line bypassing the cyclone 5.

The stream 10 coming from the concentration cyclone 5 comprises a concentrated slurry of dipotassium terephthalate in terphenyl together with byproducts. This stream 10 is combined with the gaseous stream 3 carrying the gaseous and vaporous effluent of the disproportionation reactor 1. These combined streams are conducted into a flash evaporation chamber 9 maintained under conditions to vaporize a substantial amount of the terphenyl. No additional heating of the effluents coming from the reactor 1 is necessary, and only the sensible heat of these effluents is used to effect the desired vaporization.

Inside the flash evaporation chamber 9 there is a cyclone 11 through which the vaporized terphenyl passes for disengaging from any entrained solid particles. The terphenyl vapor leaves the flash evaporation chamber in stream 12. In the lower portion 13 of the flash chamber 9, the solids are accumulated and are removed for further processing via line 14. The solids can be conducted to a solution tank and contacted with water and the resultant product can be separated and recovered (not shown).

At the base of the flash evaporation chamber 9, a gas stream 15 is introduced into said chamber. This stream 15 consists of gases and vapors such as carbon dioxide and benzene. The gas stream 15 introduced into the flash evaporation chamber 9 exerts a fluidizing action upon the solids accumulated in the lower portion 13 of said chamber 9. This fluidizing action prevents the solids from caking together and enables an easier and continuous removal of the solid products of the process. The gases used for this fluidizing action are removed from the chamber 9 as a portion of stream 12.

The stream 12 comprising the terphenyl vapor and other lighter vapors is passed through one or more zones utilizing the heat of this stream 12, such as heat exchangers 16 and 17, to produce process steam. Preferably, the first heat exchanger 16 is used to produce high-pressure steam, and the second heat exchanger 17 is used to produce low-pressure steam. The partially cooled materials of stream 12 are then conducted to a receiver and a phase separator 18 in which the condensed liquid components can be separated from the vaporous components. The vaporous components are conducted from the receiver 18 and passed via line 19 to benzene and carbon dioxide recovery systems (not shown). The hot liquid terphenyl is conducted via line 20 from receiver 18 to further processing and recycling stations (not shown).

In the drawing and the above description, many details of the apparatus, such as valves, heat exchangers, pumps, controlling means, etc., have been omitted. These items, however, are well known to one skilled in the art. Any suitable apparatus of this nature can be used.

The following calculated example is provided to illustrate the present invention as applied to the production of dipotassium terephthalate using terphenyl as dispersant and zinc benzoate as catalyst in an apparatus such as that schematically shown in the drawing.

EXAMPLE

Potassium benzoate and zinc benzoate are introduced together with terphenyl and carbon dioxide into a disproportionation reactor 1. The disproportionation reaction is carried out at about 800 psia and 850° F. The slurry effluent from the reactor 1 is concentrated in a slurry concentration cyclone 5 and the thickened slurry is combined with the overhead gaseous effluent from the reactor 1. The resulting mixture is passed into a flash evaporation chamber 9. The thickened slurry is fed to the evaporation chamber 9 at a temperature of 740° F. and the pressure inside the evaporation chamber 9 is 21 psia. Dipotassium terephthalate and other solids are removed from the flash evaporation chamber 9 at a temperature of about 653° F. Terphenyl together with other vapors are removed as an overhead from said flash evaporation chamber 9 at a temperature of 732° F. and a pressure of 20 psia. These vapors are passed through high-pressure and low-pressure steam producers 16 and 17 which cool the vapors to about 300° F. The lighter gases are separated from the reliquefied terphenyl and a portion of these gases is recycled to the flash evaporation chamber 9 for the fluidizing action as described.

In the following table, the distribution of materials in the various streams of the example described is shown. The stream numbers in the table correspond to the stream numbers in the drawing.

TABLE

| Stream No. | 3 | 4 | 6 | 10 | 15 | 14 | 12 | 20 | 19 |
|---|---|---|---|---|---|---|---|---|---|
| | | | | (Pounds per Hour) | | | | | |
| $CO_2$ | 1,000 | | | | 440 | | 1,440 | 0 | 1,000 |
| Benzene | 21,100 | | | | 7,000 | | 28,100 | 5,200 | 15,900 |
| Terphenyl | | 117,500 | 58,060 | 59,440 | 40 | | 59,480 | 59,350 | 90 |
| KBz | | 8,600 | | 8,600 | | 8,600 | | | |
| $K_2TP$ | | 75,375 | | 75,375 | | 75,375 | | | |
| ZnBz | | 5,185 | | 5,185 | | 5,185 | | | |
| | 22,100 | 206,660 | 58,060 | 148,600 | 7,480 | 89,160 | 89,020 | 64,550 | 16,990 |

KBz = Potassium benzoate $C_6H_5$-COOK
$K_2TP$ = Dipotassium terephthalate $C_6H_4$-$(COOK)_2$
ZnBz = Zinc benzoate From the data of the above-shown table, it can readily be seen that the invention process will provide a suitable and convenient means for separating the terphenyl dispersant from the dipotassium terephthalate and other solids by means of flash evaporation utilizing only the sensible heat contained in the effluents coming from the disproportionation reactor.

Reasonable variations and modifications, which will be apparent to those skilled in the art, can be made in this invention without departing from the spirit or scope thereof.

What is claimed is:

1. In a process for producing alkali metal salts of aromatic polycarboxylic acids wherein an alkali metal salt of an aromatic carboxylic acid and a dispersant are introduced into a disproportionation zone, said alkali metal salt of said aromatic carboxylic acid is disproportionated at elevated temperature and high pressure conditions whereby there is formed a slurry comprising said alkali metal salts of said aromatic polycarboxylic acid and said dispersant and a gaseous effluent and wherein said alkali metal salts and said dispersant are separated, the improvement which comprises
a. treating said slurry in a concentration zone and increasing the solids content of said slurry;
b. combining said slurry having an increased content of solids with said gaseous effluent from said reaction zone,
c. passing said slurry combined with said gaseous effluent to a separation zone;
d. suddenly lowering the high pressure of said slurry combined with said gaseous effluent to a pressure of about 10 to 100 psia,
e. recovering said dispersant as a vapor from said separation zone, and
f. recovering said alkali metal salts of said polycarboxylic acids as solids from said separation zone.

2. A process in accordance with claim 1 wherein said dispersant is selected from the group consisting of biphenyl, terphenyl, quaterphenyl, binaphthyl, isomers thereof and mixtures thereof.

3. A process in accordance with claim 1 wherein said dispersant is terphenyl.

4. A process in accordance with claim 1 wherein said alkali metal salts of polycarboxylic acids are accumulated as solids in the bottom portion of said separation zone.

5. A process in accordance with claim 1 wherein the pressure drop occurring during said step of suddenly lowering the pressure of said slurry is about 500 to 900 psi.

6. A process in accordance with claim 1 wherein said pressure drop is about 700 to 800 psi.

7. A process in accordance with claim 1 wherein said slurry to be introduced into said separation zone has a pressure of about 700 to 780 psia and the pressure in said separation zone is maintained at about 20 to 50 psia.

8. A process in accordance with claim 4 wherein a gaseous effluent comprising vapor of said dispersant is withdrawn from said separation zone and is separated into a first stream comprising said dispersant and a second gaseous stream and wherein at least a portion of said second gaseous stream is reintroduced into the bottom portion of said separation zone under such conditions that at least a partial fluidization of solids accumulating in said bottom portion is achieved.

9. A process in accordance with claim 1 wherein said alkali metal salt of said aromatic carboxylic acid is potassium benzoate, said dispersant is terphenyl and said alkali metal salt of an aromatic polycarboxylic acid is potassium terephthalate.

* * * * *